(12) United States Patent
Fernando et al.

(10) Patent No.: US 7,374,539 B2
(45) Date of Patent: May 20, 2008

(54) METHOD AND APPARATUS FOR PREDICTING MATERIAL HYPERTENSION DURING PREGNANCY USING COHERENCE ANALYSIS OF MATERIAL AND FETAL BLOOD VELOCITY WAVEFORMS

(75) Inventors: Kumari L. Fernando, Salt Lake City, UT (US); V. John Mathews, Salt Lake City, UT (US); Edward B. Clark, Salt Lake City, UT (US); Michael W. Varner, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 199 days.

(21) Appl. No.: 10/934,656

(22) Filed: Sep. 2, 2004

(65) Prior Publication Data

US 2005/0065439 A1    Mar. 24, 2005

Related U.S. Application Data

(60) Provisional application No. 60/499,699, filed on Sep. 2, 2003.

(51) Int. Cl.
*A61B 8/00* (2006.01)

(52) U.S. Cl. ........................ 600/454; 600/481

(58) Field of Classification Search ................ 600/453, 600/454, 504, 481
See application file for complete search history.

(56) References Cited

U.S. PATENT DOCUMENTS

| | | | | | |
|---|---|---|---|---|---|
| 4,355,368 | A | * | 10/1982 | Zeidler et al. | 708/422 |
| 5,146,414 | A | * | 9/1992 | McKown et al. | 702/49 |
| 5,433,204 | A | * | 7/1995 | Olson | 600/454 |
| 5,596,993 | A | * | 1/1997 | Oriol et al. | 600/511 |
| 6,024,701 | A | * | 2/2000 | Almog | 600/300 |
| 6,086,533 | A | * | 7/2000 | Madsen et al. | 600/438 |
| 6,340,346 | B1 | * | 1/2002 | Almog et al. | 600/300 |

* cited by examiner

*Primary Examiner*—Robert I. Nasser, Jr.
*Assistant Examiner*—Karen E Toth
(74) *Attorney, Agent, or Firm*—Thorpe North & Western LLP

(57) ABSTRACT

An embodiment of a method of predicting maternal hypertension during pregnancy is disclosed. The method may include measuring a maternal blood velocity waveform and measuring a fetal blood velocity waveform. The method may further include the calculation of a coherence value using a magnitude-squared coherence function between the maternal and fetal blood velocity waveforms and comparing the coherence value to a predetermined threshold value.

10 Claims, 9 Drawing Sheets

TABLE 1

PERFORMANCE ANALYSIS.

| Experiment | $\mu_{\tilde{\gamma}th}$ | $\sigma^2_{\tilde{\gamma}th}$ | $P_{sen}$ % | $P_{spe}$ % | $P_{sen}$ % | $P_{spe}$ % |
|---|---|---|---|---|---|---|
| 1. $\omega_1 = 5$, $\omega_2 = 4$ | -0.0014 | $1.2 \times 10^{-4}$ | 81.85 | 58.54 | 86.30 | 50.74 |
| 2. 80% sensitivity | -0.016 | $4.8 \times 10^{-4}$ | 80.00 | 58.80 | 85.00 | 53.52 |

METHOD AND APPARATUS FOR PREDICTING MATERIAL HYPERTENSION DURING PREGNANCY USING COHERENCE ANALYSIS OF MATERIAL AND FETAL BLOOD VELOCITY WAVEFORMS

This non-provisional application claims priority to U.S. application No. 60/499,699 filed Sep. 2, 2003.

This application is funded from a Predoctoral Fellowship from the American Heart Association, grant number 0110005Y.

BACKGROUND OF THE INVENTION

1. Field of the Invention

This patent application is related to the field of signal processing. More particularly, the invention relates to the use of ultrasound Doppler measurements.

2. Related Art

Preeclampsia is a major cause of maternal mortality as well as perinatal morbidity and mortality. It is mainly characterized by hypertension and protienuria. Preeclampsia affects as many as one in ten of all pregnancies if its milder forms are counted. The incidence of preeclampsia is higher in women who are nulliparous, carry multiple fetuses, have chronic hypertension, diabetes, or if the woman has had previous preeclamptic pregnancies. Although clinical manifestations do not appear until the final three months, the foundations for preeclampsia are thought to be established in the first 10-12 weeks of gestation.

Maternal complications due to preeclampsia are associated with the vascular system. Mothers are at risk for intravascular coagulation, bleeding, and organ failure. Maternal blood volume is reduced and has altered distribution. The treatment of hypertension in pregnancy does not eliminate or reverse the process but does help prevent maternal cardiovascular complications, especially during labor and delivery.

Evidence exists to suggest that there is inadequate trophoblast secondary invasion in pregnancies that later developed preeclampsia. The adaptation to a limited supply of nutrients due to inadequate secondary trophoblast invasion in preeclampsia may lead to damages in the structure and the metabolism of a fetal life. Suboptimum supply of oxygen and nutrients may also lead to fetal intrauterine growth restriction. This, together with premature delivery, poses major threats to the fetus leading to various degrees of morbidity and even death. Long term follow up studies have demonstrated that babies who have suffered intrauterine growth retardation and those who are small and disproportionate at birth are more likely to develop hypertension, coronary heart disease and non-insulin-dependent diabetes in adult life. These observations suggest that fetuses are quite sensitive to the maternal placental function.

Various methods have been developed to detect preeclamptic pregnancies early in the gestational period. The use of ambulatory pressure monitoring for identifying hypertensive pregnancies has been used. Using this method, blood pressure monitoring can be performed in four-week intervals for 48 hours throughout gestation starting in the 16th week. Ambulatory pressure monitoring has shown significant results with specificity and sensitivity above 90%. However, the instrumentation required for pressure monitoring is expensive and reported lower acceptability and sleep disturbances among patients.

Doppler ultrasound blood velocity waveforms have also been employed for predicting preeclampsia. A uterine arterial pulsatility index (PI) has been studied as an indicator to the increased resistance to the placental flow during the $11^{th}$ through $14^{th}$ week and $23^{rd}$ week of gestation in various studies using Doppler ultrasound measurements. Analysis of the Doppler ultrasound measurements has proven difficult, however. Current techniques to analyze the measurements have resulted in sensitivities of mean PI for preeclampsia at rates as low as 25-27% during 1-14 weeks and 41% at 23 weeks. Superior techniques for analyzing data from Doppler ultrasound measurements are greatly desired.

SUMMARY OF THE INVENTION

Embodiments of a method and apparatus for predicting maternal hypertension during pregnancy using coherence analysis of maternal and fetal blood velocity waveforms are disclosed.

An embodiment of a method for predicting maternal hypertension during pregnancy is disclosed. The method may include measuring a maternal blood velocity waveform and measuring a fetal blood velocity waveform. The method may further include the calculation of a coherence value using a magnitude-squared coherence function between the maternal and fetal blood velocity waveforms and comparing the coherence value to a predetermined threshold value.

An embodiment of an apparatus for predicting maternal hypertension during pregnancy is also disclosed. The apparatus may include a sensor for measuring a maternal blood velocity waveform and a sensor for measuring a fetal blood velocity waveform. The apparatus may further include a processor in communication with the sensors for calculating a coherence value using a magnitude-squared coherence function between the maternal and fetal blood velocity waveforms and comparing the coherence value to a predetermined threshold value.

Additional features and advantages of the invention will be apparent from the detailed description which follows, taken in conjunction with the accompanying drawings, which together illustrate, by way of example, features of embodiments of the present invention.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 9 shows a table containing test data.

Reference will now be made to the exemplary embodiments illustrated, and specific language will be used herein to describe the same. It will nevertheless be understood that no limitation or the scope of the invention is thereby intended.

DETAILED DESCRIPTION OF EXAMPLE EMBODIMENT(S)

Figure 1:
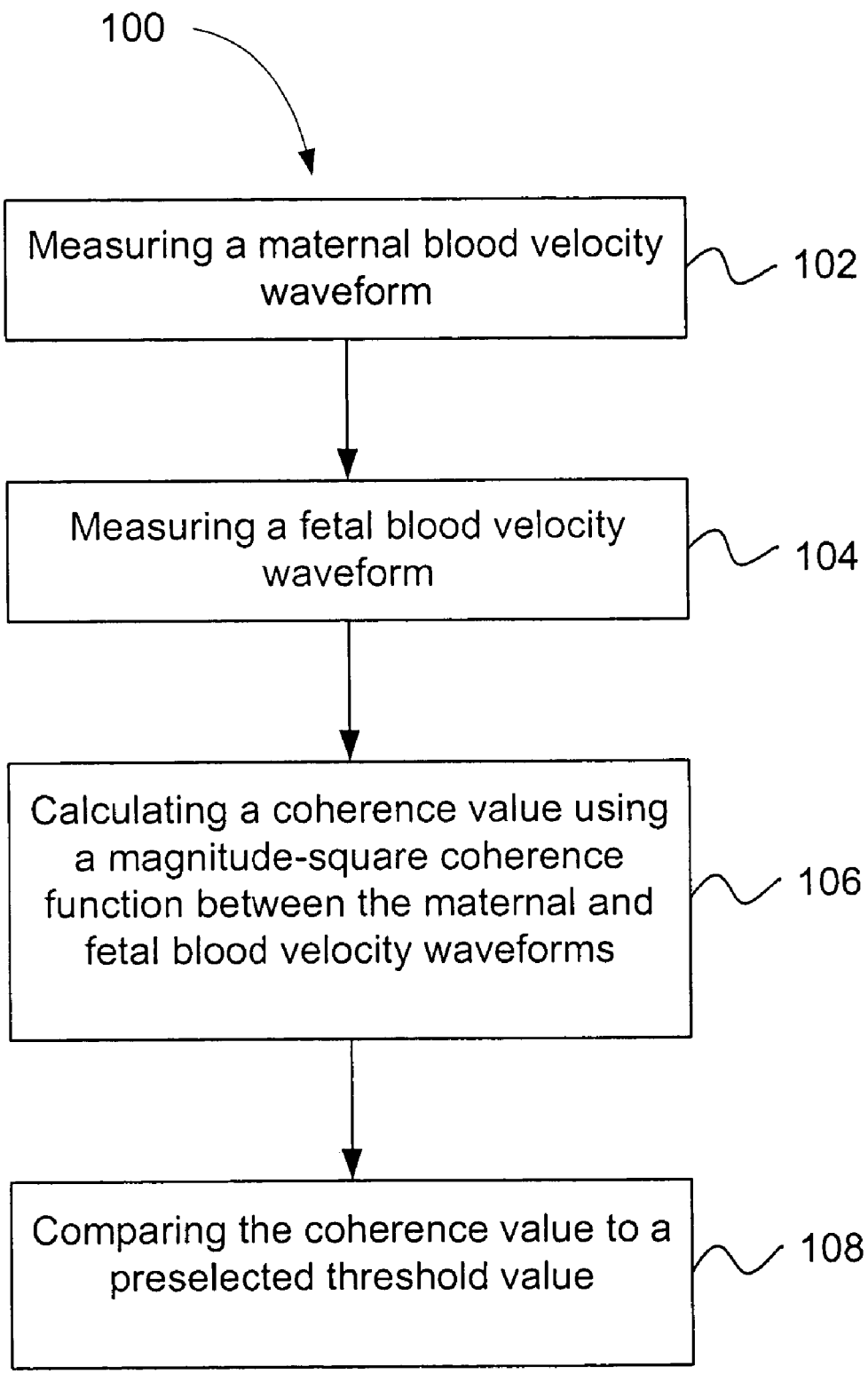
FIG. 1 is a flow diagram of a method for predicting maternal hypertension during pregnancy in accordance with an embodiment of the present invention.

FIG. 1 is a flow diagram of a method 100 of predicting maternal hypertension during pregnancy in accordance with an embodiment of the present invention. The method 100 may include measuring 102 a maternal blood velocity waveform and measuring 104 a fetal blood velocity waveform. The measuring steps 102, 104, may be performed sequentially in any order or in a presently preferred embodiment, simultaneously as shown in FIG. 1. This method may further include calculating 106 a coherence value using a magnitude-squared coherence (MSC) function between the maternal and fetal blood velocity waveforms. An operation in the method may further include comparing 108 the coherence value to a predetermined threshold value. Such a method may be contained in computer instructions suitable for implementation in computer hardware, software or firmware according to embodiments of the present invention.

Figure 2:
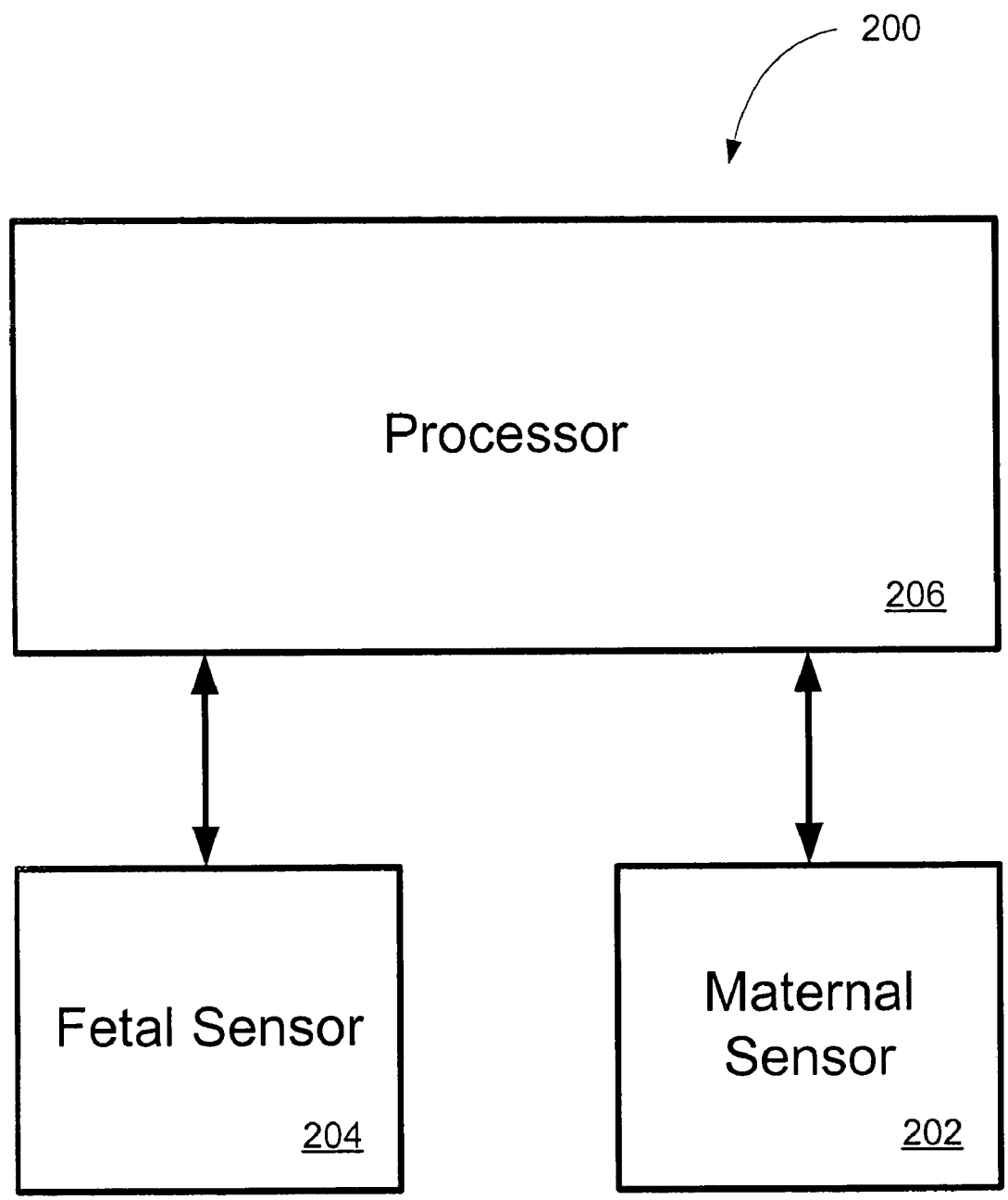
FIG. 2 is a block diagram of an apparatus for predicting maternal hypertension during pregnancy in accordance with an embodiment of the present invention.

FIG. 2 is a block diagram of an apparatus 200 for predicting maternal hypertension during pregnancy in accordance with an embodiment of the present invention. The apparatus 200 may include a maternal sensor 202 for measuring a maternal blood velocity waveform and a fetal sensor 204 for measuring a fetal blood velocity waveform. The sensors 202, 204 may be Doppler ultrasound sensors or any other sensor capable of detecting blood velocity waveforms. A processor 206 can be in communication with the sensors 202, 204 and be configured for calculating a coherence value using a magnitude-squared coherence function between the maternal and fetal blood velocity waveforms. The coherence value can be compared to a predetermined threshold value. Processor 206 may be a general-purpose microprocessor such as a central processing unit (CPU), a digital signal processor (DSP), a reconfigurable field programmable gate array (FPGA) such as a Xilinx programmable logic device, a general-purpose computer or any other computer hardware with or without software or firmware for performing the calculations specified herein.

Yet another embodiment of the present invention includes a processor 206 configured to receive maternal and fetal blood velocity waveforms as input and to calculate a coherence value using a magnitude-squared coherence function between the maternal and fetal blood velocity waveforms and comparing the coherence value to a predetermined threshold value. This embodiment could be configured to receive input from one or more Doppler ultrasound machines.

One embodiment of apparatus 200 contemplates the simultaneous measurement of maternal and fetal blood velocity waveforms. However, sequential and time delayed measurement of maternal and fetal blood velocity waveforms are also contemplated to be within the scope of the present invention and for use with the method and apparatus described above. Experimental results using sequential measurement of maternal and fetal blood velocity waveforms are described below.

The main advantages of this coherence analysis for the prediction of preeclampsia are: 1) it can be used to identify women at risk for hypertensive disorders at an earlier stage of pregnancy than currently possible, 2) it is non-invasive and simple to perform, and 3) it is highly sensitive.

Physiology Related to Development of Preeclampsia

Prior to implantation, the cells of the early embryo separate into two types, the inner cell mass and the outer cells. The inner cell mass becomes the fetus and its protective membranes, and the outer cells are collectively known as the trophoblast. The trophoblast is the only embryonic tissue that comes into contact with maternal tissues. Its main purpose is to form the placenta that juxtaposes the maternal and fetal circulations. A secondary function of the trophoblast is to engineer structural changes in the maternal blood vessels terminating in the placenta bed, so that they can carry a substantial volume of blood to the placenta. These vessels are known as spiral arteries due to their coiled shape.

The transformation of the spiral arteries takes place in two phases. During the primary trophoblast invasion within the first few weeks after implantation, the endometrial blood vessels are converted to the uteroplacental vessels. In the second phase, between 12 to 18 weeks of pregnancy, the trophoblast invades more deeply into the segments of the vessels within the uterine muscle and further increases their capacity. The secondary trophoblast invasion results in an increase in the vessel diameter and a decrease in the vessel wall thickness. When there is inadequate trophoblast invasion, the spiral artery remains narrow and its walls thicken. This results in reduced blood flow to the intervillos space. The inadequacy of secondary trophoblast invasion results in a spectrum of pregnancy complications including maternal hypertension and preeclampsia.

There is evidence that absence of or inadequate secondary trophoblast invasion can contribute to the development of hypertensive disorders later in human pregnancy. The functional relationship between the maternal and fetal blood flows may be different in normotensive and hypertensive pregnancies. Furthermore, the secondary trophoblast invasion in the placental function typically occurs by the $12^{th}$ week of gestation. This can make it possible to detect hypertensive pregnancies through the analysis of maternal-fetal blood flows as early as the late first or the early second trimesters of pregnancy.

Doppler Ultrasound Techniques

Blood flow velocity waveforms can be measured from fetal arteries as early as the eighth week of gestation using transvaginal Doppler Ultrasound techniques. Ultrasonography can be a safe, noninvasive, and cost effective tool for monitoring the fetal cardiovascular system through imaging and blood velocity measurements. However, exposure to ultrasound beam for long durations of time may cause temperature increase and damage in fetal tissues, especially in the brain encased in the fetal skull. Consequently, long term monitoring of blood velocity waveforms is not recommended.

The blood velocity waveforms estimated by the use of the Doppler ultrasound techniques can be modeled as a single sinusoid embedded in white noise over short intervals of time. Such an inference can be justified when considering the autocovariance function of the signal, which matches the sinusoidal model. Therefore, the blood velocity waveforms can be modeled as a pure sinusoid embedded in white noise over short intervals.

In Doppler Ultrasonography, a beam of ultrasound is transmitted toward the blood flow whose velocity is being estimated, and it is backscattered mainly by the red blood cells of the flow. The frequency difference between the transmitted and backscattered waves is the Doppler shift, and is directly proportional to the relative velocity between the reflective interface and the receiver. The velocity is estimated using the relationship $$v = \frac{cf}{2f_0\cos\theta},$$

where c is the velocity of the ultrasound in the medium in meters/sec, f is the Doppler shift frequency in Hz, $f_o$ is the frequency of the incident ultrasound beam in Hz, and $\theta$ is the angle of incidence in radians.

Reconstruction of Maximum Blood Flow Velocity

Doppler insonation of the blood vessel produces a spectrum of frequencies. The maximum frequency of the Doppler spectrum, $f_{max}$ is proportional to the maximum blood flow velocity. In current practice, the maximum frequency waveform is estimated as the largest frequency value at which the Doppler spectrum exceeds a predetermined threshold. The most common method for estimating the maximum frequency waveform takes the largest frequency value that exceeds a certain threshold level. There are four main variations of this method including (i) the percentile method, (ii) D'Alessio's threshold crossing method, (iii) the modified threshold crossing method, and (iv) the hybrid method.

The percentile method uses the integrated Doppler power spectrum defined as $$\phi(f) = \int_0^f S(\lambda)d\lambda,$$

where S(f) is the power spectrum at frequency f. In this method the maximum frequency $f_{max}$ is defined as the frequency at which $$\phi(f_{\max}) = \frac{100-\alpha}{100}\phi_T,$$

where $\Phi_T$ is the total signal power and $\alpha(0<\alpha<100)$ is a designed parameter whose optimum value depends on both the signal-to-noise ratio (SNR) and the signal bandwidth.

Both the D'Alessio's method and the modified threshold crossing method compare the estimated power spectrum in a sliding window of r successive frequency bins to a chosen threshold level. The highest frequency that exceeds the threshold is recorded for each window for which the threshold is exceeded in at least m consecutive bins. The maximum value of this sequence of recorded frequencies is selected as the maximum frequency $f_{max}$. The threshold level in the modified threshold crossing method is chosen as a multiple of the noise density estimated as the average value of the Doppler spectrum over high frequency values where the noise components predominate.

In the hybrid algorithm, the noise density is estimated as the gradient of the integrated spectrum in the high frequency range. The maximum frequency is then estimated as the frequency at which the straight line that passes through the maximum point of the integrated spectrum at a gradient greater than the estimated noise density intersects the integrated spectrum. These maximum frequency estimation methods depend on arbitrarily selected parameters, and the estimated root-mean-square (RMS) error varies significantly with both the SNR and the bandwidth of the signal and was greater than 4% of the $f_{max}$ even at SNR values greater than 9 dB.

A geometric method, wherein maximum frequency estimation algorithms are based on the geometry of the integrated spectrum, worked better in experiments than both the percentile method and the modified threshold crossing method in experiments. The geometric method first estimates the mode frequency, the frequency at which the signal has maximum power. A reference line is then drawn connecting the points on the integrated spectrum at the estimated mode frequency and the highest frequency value (half the sampling frequency in digitized signals). The maximum frequency is then estimated as the frequency at which the Euclidean distance from this reference line to the spectrum is maximum. The geometric method has been shown to work well for Gaussian shaped spectra where the maximum frequency is relatively far away from the mode frequency, but it fails when the mode frequency is close to the maximum frequency or when the spectrum is relatively flat. It has also been shown that the estimated maximum frequency using the geometric method is susceptible to amplifier gain.

A modified geometrical method can also be implemented wherein the reference line is selected from the first point or origin of the integrated spectrum to its maximum point. The maximum frequency is estimated as the frequency corresponding to the maximum vertical distance from the reference line to the integrated spectrum. This method showed good performance in experiments. A proof of the optimality rotated integrated spectrum based methods is below.

Let $$y(n)=x(n)+\eta(n)$$

represent the digitized Doppler signal at time n, where x(n) is the signal of interest and $\eta(n)$ is a zero-mean and white noise process with variance $\sigma_\eta^2$. Let $f_N$ denote the Nyquist frequency (half the sampling frequency) of the signal. Assuming that x(n) is band limited to the frequency $f_{max}$, where $f_{max}<f_N$.

The integrated spectrum of the signal component x(n) is given by $$\phi_x(f) = \int_0^f S_x(\lambda)d\lambda,$$

where $S_x(f)$ is its power spectrum at frequency f. The integrated spectrum of y(n) is given by $$\phi_Y(f)=\phi_X(f)+\sigma_\eta^2 f.$$

Since x(n) is band-limited to $f_{max}$, for frequencies $f>f_{max}$, $$\phi_Y(f)=\phi_X(f_{max})+\sigma_\eta^2 f.$$

Figure 3:
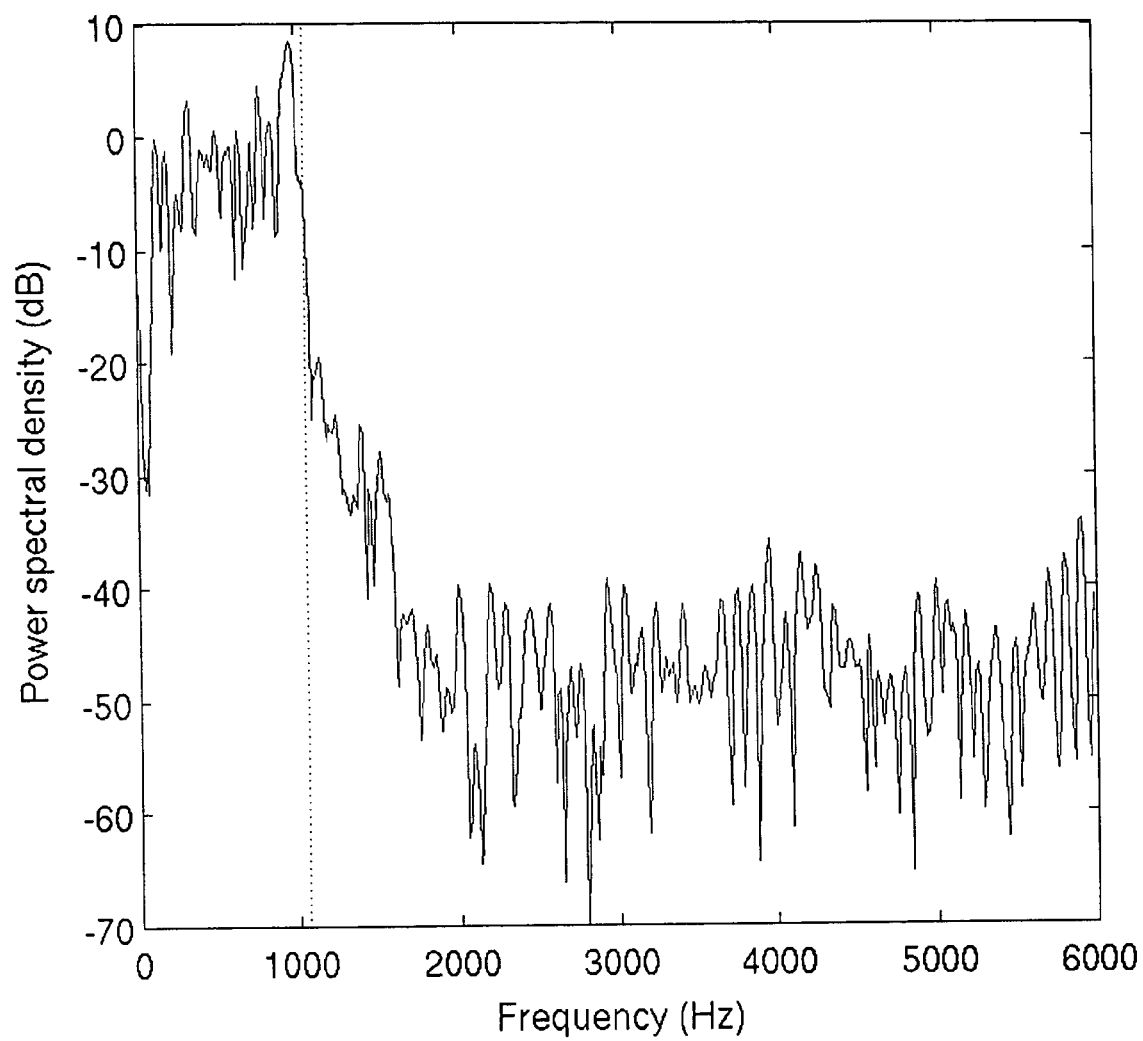
FIG. 3 shows the estimated spectrum of a segment of Doppler signal recorded from an 18 week old fetus.
Figure 4:
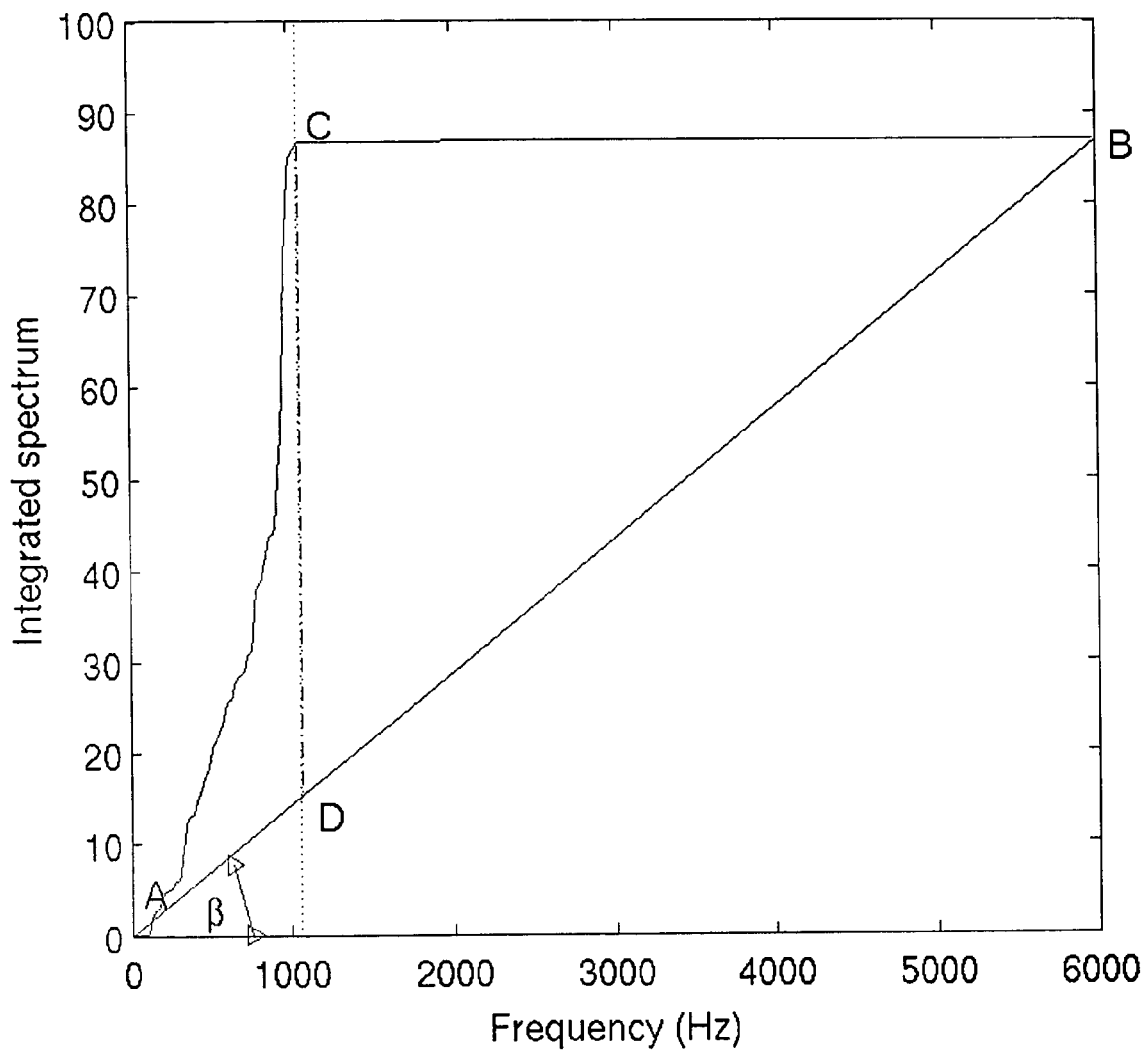
FIG. 4 shows the integrated spectrum of the signal in FIG. 3.

An example of the estimated spectrum of a portion of a Doppler signal recorded from the umbilical artery of an 18 week old fetus and the corresponding integrated spectrum are depicted in FIGS. 3 and 4 respectively. The power spectrum was estimated as the periodogram of a Hann-windowed 512-sample segment of data. The FFT size was 1024 samples.

The Gradient of the integrated spectrum $$\frac{\partial\phi_Y(f)}{\partial f}$$

in the frequency range $f_{max}<f<f_N$ corresponds to the instantaneous noise density. The average gradient of the integrated spectrum within the signal bandwidth is greater than the noise density. An estimate of the maximum Doppler frequency can be found using the following method. The integrated Doppler spectrum can be rotated over the frequency to obtain $$\phi_{rot}(f) = \phi_Y(f)\cos\beta - f\sin\beta,$$

where $\beta$ is the angle of rotation. For $0<\beta<\pi/2$, dividing both sides by $\cos\beta$ results in $$\hat{\phi}_{rot}(f) = \phi_Y(f) - f\tan\beta.$$

It is straightforward to show that $\phi_{rot}(f)$ and $\hat{\phi}_{rot}(f)$ peak at the same frequency.

In the modified geometric method, a straight line can be drawn connecting the origin to the maximum value of the integrated spectrum as shown by the segment AB in FIG. 4. The frequency at which the vertical distance from this straight line to the integrated spectrum is maximum (CD) is the estimate of the maximum Doppler shift. Therefore, the vertical distance between the integrated spectrum and the straight line AB at any frequency f is given by $$\hat{\phi}_{rot}(f) = \phi_Y(f) - f\tan\beta,$$

where $$\tan\beta = \frac{\phi_Y(f_N)}{f_N} = \frac{\phi_X(f_{\max})}{f_N} + \sigma_\eta^2.$$

It is clear that the modified geometric method is a special case of the rotated integrated spectrum in which the angle of rotation is given by the above equation. The maximum vertical distance occurs at the maximum Doppler shift for angles that satisfy the following smoothness constraint:

$$\frac{\phi_X(f_{\max})}{f_N} < \frac{\phi_X(f_{\max}) - \phi_X(f)}{f_{\max} - f}; \; 0 \le f \le f_{\max}.$$

This condition implies that the average spectrum of the input signal over the whole frequency range is smaller than the average spectrum computed in any interval in which the signal is present. This is a smoothness condition which constrains the signal spectrum to be relatively flat and not to exhibit significant dynamics over its bandwidth. For lowpass signals such that $f_N \gg f_{max}$ this assumption is satisfied easily in most practical situations.

The maximum velocity reconstruction algorithm is based on the following lemma.

Lemma: for signal spectra satisfying $\phi_Y(f) = \phi_X(f) + \sigma_\eta^2 f$ the maximum value of $\hat{\phi}_{rot}(f)$ defined above as $$\hat{\phi}_{rot}(f) = \phi_Y(f) - f\tan\beta$$

occurs at the maximum Doppler shift for any angle of rotation $\beta$ that satisfies $$\sigma_\eta^2 < \tan\beta \le \frac{\phi_X(f_{\max})}{f_N} + \sigma_\eta^2.$$

The lower limit of $\tan\beta$ is chosen such that it is greater than the noise density. This ensures that the rotated integrated spectrum is no longer a monotonically increasing function. Theoretically, $f_{max}$ can take any value between 0 and $f_N$. Therefore, the maximum limit of the angle of rotation can be chosen such that the reference line passing through the origin and drawn at an angle $\beta$ to the frequency axis does not intersect the integrated spectrum at any frequency value less than $f_N$. The maximum Doppler frequency can then be estimated as the frequency at which $\hat{\phi}_{rot}(f)$ peaks. The lemma can be proved by contradiction:

As can be seen from $$\tan\beta = \frac{\phi_Y(f_N)}{f_N} = \frac{\phi_Y(f_{\max})}{f_N} + \sigma_\eta^2,$$

the modified geometric method rotates the integrated spectrum by the maximum allowed angle in $$\sigma_\eta^2 < \tan\beta \le \frac{\phi_X(f_{\max})}{f_N} + \sigma_\eta^2.$$

Consequently, the frequency estimation using this approach can provide accurate results. This, combined with the ease of implementing the rotation, makes the maximum allowed rotation an excellent choice for maximum velocity estimation.

Reconstruction of Mean Blood Velocity Waveforms

In many applications, the power-weighted mean frequency of a signal x(n) defined as $$\overline{\omega} = \frac{\int_{\omega_{\min}}^{\omega_{\max}} \omega S_x(\omega) d\omega}{\int_{\omega_{\min}}^{\omega_{\max}} S_x(\omega) d\omega},$$

where $S_x(\omega)$ is the power spectrum of x(n) at the frequency $\omega$, and $\omega_{min}$ and $\omega_{max}$ are respectively the minimum and maximum frequencies of the input signal. In current practice, the mean frequency estimation involves three steps: (i) estimate the power spectrum of the input signal, (ii) evaluate the minimum and the maximum frequency values, and (iii) compute the mean frequency using the above equation. Generally, the power spectrum has been estimated using a fast Fourier transform (FFT) algorithm. Once the spectrum is estimated, a threshold level is chosen manually such that it is larger than the noise level. The lowest and the highest frequency values at which the spectral powers equal the threshold level are selected as the minimum and the maximum signal frequencies.

A method which may be superior to using an FFT is the Pisarenko harmonic decomposition algorithm (PHD), wherein the single frequency approximation for a narrowband lowpass signal embedded in white noise using PHD is approximately the power-weighted mean frequency of the signal. In preliminary analysis, only signals whose bandwidth and maximum frequency were much smaller than the sampling frequency of thee digitized signal were used. However, experimental results show that the approximation is valid for signals up to one-fourth of the sampling frequency.

The estimation for complex-valued signals will first be shown and then it will be extended to real-valued signals. For complex-valued signals, let $$y(n) = x(n) + \eta(n),$$

represent the input signal, where x(n) is the signal of interest and η(n) is an additive circular white noise process with zero-mean value and variance $\sigma_\eta^2$. Here, x(n) is a zero-mean, complex-valued narrowband signal whose bandwidth is much smaller than the sampling frequency. The covariance function $r_X(k)$ of x(n) is related to its power spectrum $S_X(\omega)$ through the expression $$r_X(k) = \frac{1}{2\pi} \int_{\omega_{min}}^{\omega_{max}} S_X(\omega) e^{j\omega k} d\omega,$$

where $\omega_{min}$ and $\omega_{max}$ are respectively, the minimum and the maximum frequencies at which the signal x(n) is present. Consider the 2×2-element covariance matrix of the input signal given by $$R_Y = \begin{bmatrix} r_X(0) + \sigma_\eta^2 & r_X(1) \\ r_X^*(1) & r_X(0) + \sigma_\eta^2 \end{bmatrix},$$

where $r^*_X(1)$ represents the complex conjugate of $r_X(1)$. The eigenvalues of $R_Y$ are $$\lambda_1 = r_X(0) + \sigma_\eta^2 + |r_X(1)|,$$

and $$\lambda_2 = r_X(0) + \sigma_\eta^2 - |r_X(1)|.$$

The eigenvector corresponding to the smallest eigenvalue $\lambda_2$ is $$g = m\left[-\frac{r_X(1)}{|r_X(1)|} \quad 1\right]^T,$$

where m is an arbitrary constant.

Now, following the method employed in PHD to estimate the frequency of a single sinusoid that best represents $R_Y$, let $w = [1 \ e^{j\hat{\omega}}]^H$, where $\hat{\omega}$ is the value of the single frequency that satisfies the condition $w^H g = 0$ and $(\cdot)^H$ and $(\cdot)^H$ denotes the Hermitian of the matrix or vector $(\cdot)$. It can be easily shown that $w^H g$ can take the value of zero for an appropriate choice of $\hat{\omega}$. Substituting for w and g we get $$[1 \ e^{j\hat{\omega}}]\left[-\frac{r_X(1)}{|r_X(1)|} \quad 1\right]^T = -\frac{r_X(1)}{|r_X(1)|} + e^{j\hat{\omega}} = 0.$$

From this we can write $$\hat{\omega} = \angle \frac{r_X(1)}{|r_X(1)|}.$$

The frequency represented by the phase angle of the autocovariance value at lag one of a complex-valued signal is the power weighted mean frequency of the signal. Therefore, the final equation above represents the power weighted mean frequency of the input signal x(n).

Considering the input signal x(n) with both narrowband and lowpass characteristics, for real-valued signals the covariance function $r_X(k)$ of x(n) is related to the power spectrum $S_X(\omega)$ by $$r_X(k) = \frac{1}{\pi} \int_{\omega_{min}}^{\omega_{max}} S_X(\omega) \cos(k\omega) d\omega,$$

where $\omega_{min}$ and $\omega_{max}$ are respectively, the minimum and the maximum frequencies of the signal. Since each real-valued sinusoid can be represented by two complex-valued sinusoids, 3×3-element covariance matrices are considered. The 3×3-element covariance matrix of y(n) is $$R_Y = \begin{bmatrix} r_x(0) + \sigma_\eta^2 & r_x(1) & r_x(2) \\ r_x(1) & r_x(0) + \sigma_\eta^2 & r_x(1) \\ r_x(2) & r_x(1) & r_x(0) + \sigma_\eta^2 \end{bmatrix},$$

and its eigenvalues are $$\lambda_1 = r_x(0) + \sigma_\eta^2 + \frac{1}{2}\left(r_x(2) + \sqrt{r_x^2(2) + 8r_x^2(1)}\right),$$

$$\lambda_2 = r_x(0) + \sigma_\eta^2 - r_x(2),$$

and $$\lambda_3 = r_x(0) + \sigma_\eta^2 + \frac{1}{2}\left(r_x(2) - \sqrt{r_x^2(2) + 8r_x^2(1)}\right).$$

Considering lowpass signals such that $|r_x(1)| > r_x(2)$, the eigenvector corresponding to the smallest eigenvalue $\lambda_3$ is $$g = m\left[1 \quad -\frac{4r_x(1)}{\sqrt{r_x^2(2) + 8r_x^2(1)} - r_x(2)} \quad 1\right]^T,$$

where m is an arbitrary constant.

The solution to the relationship $w^H g = 0$, where $w = [1 \ e^{j\hat{\omega}} \ e^{j2\hat{\omega}}]^H$ yields $$\cos\hat{\omega} = \frac{2r_x(1)}{\sqrt{r_x^2(2) + 8r_x^2(1)} - r_x(2)}.$$

Substituting for $r_X^2(2) + 8r_X^2(1)$ gives $$r_X^2(2) + 8r_X^2(1) = \left(\int_{\omega_{min}}^{\omega_{max}} S_X(\omega)\cos 2\omega d\omega\right)^2 +$$

$$8\left(\int_{\omega_{min}}^{\omega_{max}} S_X(\omega)\cos\omega d\omega\right)^2,$$

$$= \int_{\omega_{min}}^{\omega_{max}}\int_{\omega_{min}}^{\omega_{max}} S_X(\omega)S_X(\lambda)\cos 2\omega \cos 2\lambda d\omega d\lambda +$$

-continued $$8\int_{\omega_{min}}^{\omega_{max}}\int_{\omega_{min}}^{\omega_{max}} S_X(\omega)S_X(\lambda)\cos\omega\cos\lambda d\omega d\lambda,$$

$$=\int_{\omega_{min}}^{\omega_{max}}\int_{\omega_{min}}^{\omega_{max}} S_X(\omega)S_X(\lambda)((2\cos^2\omega-1)$$

$$(2\cos^2\lambda-1)+8\cos\omega\cos\lambda)d\omega d\lambda,$$

$$=\int_{\omega_{min}}^{\omega_{max}}\int_{\omega_{min}}^{\omega_{max}} S_X(\omega)S_X(\lambda)(4\cos^2\omega\cos^2\lambda-$$

$$2(\cos^2\omega+\cos^2\lambda)+8\cos\omega\cos\lambda+1)d\omega d\lambda.$$

For narrowband signals for which $(\omega_{max}-\omega_{min})$ is small, $(\cos\omega-\cos\lambda)^2 \approx 0$. Therefore, for $\omega_{min} \leq \omega, \lambda \leq \omega_{max}$ $$\cos^2\omega+\cos^2\lambda \approx 2\cos\omega\cos\lambda,$$

and $$8\cos\omega\cos\lambda-2(\cos^2\omega+\cos^2\lambda)\approx 2(\cos^2\omega+\cos^2\lambda).$$

Substitution yields $$\cos\hat\omega \approx \frac{\int_{\omega_{min}}^{\omega_{max}} S_X(\omega)\cos\omega d\omega}{\int_{\omega_{min}}^{\omega_{max}} S_X(\omega)d\omega}.$$

That is $$\cos\hat\omega \int_{\omega_{min}}^{\omega_{max}} S_X(\omega)d\omega \approx \int_{\omega_{min}}^{\omega_{max}} S_X(\omega)\cos\omega d\omega.$$

Dividing both sides by $\cos\hat\omega$ results in $$\int_{\omega_{min}}^{\omega_{max}} S_X(\omega)d\omega \approx \int_{\omega_{min}}^{\omega_{max}} S_X(\omega)\frac{\cos\omega}{\cos\hat\omega}d\omega.$$

Multiplying the numerator and the denominator with $\sin\hat\omega$ gives $$\int_{\omega_{min}}^{\omega_{max}} S_X(\omega)d\omega \approx \int_{\omega_{min}}^{\omega_{max}} S_X(\omega)\frac{\cos\omega\sin\hat\omega}{\cos\hat\omega\sin\hat\omega}d\omega.$$

Since $(\omega_{max}-\omega_{min})$ is small and $\omega_{min} \leq \omega \leq \omega_{max}$, $(\omega+\hat\omega)\approx 2\hat\omega$ and $\sin(\omega-\hat\omega)\approx(\omega-\hat\omega)$. Therefore, $$\frac{\cos\omega\sin\hat\omega}{\cos\hat\omega\sin\hat\omega} = \frac{0.5\sin(\omega+\hat\omega)-0.5\sin(\omega+\hat\omega)}{0.5\sin 2\hat\omega}$$

$$\approx 1 - \frac{\omega+\hat\omega}{\sin 2\hat\omega}.$$

Substitution gives $$\int_{\omega_{min}}^{\omega_{max}} S_X(\omega)d\omega \approx \int_{\omega_{min}}^{\omega_{max}} S_X(\omega)\left[1-\frac{\omega-\hat\omega}{\sin 2\hat\omega}\right]d\omega,$$

implying that $$\int_{\omega_{min}}^{\omega_{max}} S_X(\omega)\frac{(\omega-\hat\omega)}{\sin 2\hat\omega}d\omega \approx 0.$$

Since $2\hat\omega \neq 0$, solving for $\hat\omega$ yields $$\hat\omega \approx \frac{\int_{\omega_{min}}^{\omega_{max}} S_X(\omega)\omega d\omega}{\int_{\omega_{min}}^{\omega_{max}} S_X(\omega)d\omega}.$$

According to the above derivation, the single frequency estimation for a real-valued narrow-band lowpass signal using the eigendecomposition of the 3×3 element covariance matrix is approximately equal to the power-weighted mean frequency of the signal. Experimental results of this method indicate that it is relatively unbiased and provides accurate results for SNRs above 0 dB.

Magnitude Squared Coherence Function and Coherence Value

The maternal blood flow is a driving force to the placental-fetal system. Therefore, functional or structural changes that affect the maternal circulation should affect the flow through the uterine artery and the flow through spiral arteries. In addition to the inadequate secondary trophoblast invasion and impaired spiral arterial blood flow, in preeclamptic pregnancies there are significant lesions in the maternal uteroplacental blood flow resulting in increased placental insufficiency. It has been implied that the relationship of maternal-fetal blood flow may be impaired in preeclamptic pregnancies due to the changes in the maternal blood flow. Such changes will be most prominent in the frequency domain at the maternal heart rate, since the maternal blood flow drives the placental-fetal circulation system. Therefore, the magnitude-square coherence function (MSC) can be used to analyze differences between the uterine and umbilical blood velocity waveforms at the maternal heart rate. Here, the MSC function is always less than one because the fetal cardiovascular system is independently controlled by its autonomic nervous system.

Mathematically, the MSC function $|\gamma(\omega)|^2$ of the two blood velocity waveforms x(n) and y(n) at frequency $\omega$ is given by $$|\gamma(\omega)|^2 = \frac{|S_{xy}(\omega)|^2}{S_{xx}(\omega)S_{yy}(\omega)},$$

where $S_{xy}(\omega)$ is the cross-spectrum, and $S_{xx}(\omega)$ and $S_{yy}(\omega)$ are the power spectra of x(n) and y(n) respectively. The MSC is a function with values between 0 and 1 that indicates how well two waveforms correspond to each other in the frequency domain. If the two signals are linearly related, the coherence value can be equal to one. If the two signals are uncorrelated, the coherence between the two signals can be equal to zero and it can be less than one for non-linearly related signals. Similarly, the coherence value can be less than one whenever uncorrelated noise is present in the two signals.

The cross spectrum between x(n) and y(n) at frequency ω is estimated by taking the Fourier transform of the cross-correlation function, and is given by $$S_{xy}(\omega) = \sum_{k=-(N-1)}^{N-1} \hat{r}_{xy}(k) e^{-j\omega k}$$

where $\hat{r}_{xy}(k)$ is the estimated value of the crosscorrelation function between x(n) and y(n) at lag k, N is the number of lag values used in estimating the cross spectrum. The crosscorrelation function between the two signals is estimated as $$\hat{r}_{xy}(k) = \frac{1}{M} \sum_{n=1}^{M} x(n) y(n-k)$$

where M is the number of samples of the data sequences employed to make the estimate.

The power spectrum of x(n) is estimated as $$S_{xx}(\omega) = \sum_{k=-(N-1)}^{N-1} \hat{r}_{xx}(k) e^{-j\omega k}$$

where $\hat{r}_{xx}(k)$ is the autocorrelation function of x(n) given by $$\hat{r}_{xx}(k) = \frac{1}{M} \sum_{n=1}^{M} x(n) x(n-k).$$

Similarly, the power spectrum of y(n) is estimated as $$S_{yy}(\omega) = \sum_{k=-(N-1)}^{N-1} \hat{r}_{yy}(k) e^{-j\omega k}$$

where $\hat{r}_{yy}(k)$ is the autocorrelation function of y(n) given by $$\hat{r}_{yy}(k) = \frac{1}{M} \sum_{n=1}^{M} y(n) y(n-k).$$

Predetermined Threshold

An optimum threshold level that can be employed to identify pregnancies at risk for subsequent hypertension from normotensive pregnancies can be determined using an algorithm and is selected such that it maximizes the weighted sum of the sensitivity and the specificity of the algorithm. Sensitivity measures the proportion of the diseased subjects correctly identified by the test. Specificity of the test measures the proportion of the normal subjects correctly identified by the test. In order to select the threshold value that is applicable to all gestational ages, the gestational age dependent mean distribution is first removed from the estimated MSC $\gamma(\omega_o)$) values. We denote the mean removed values of $\gamma(\omega_o)$ as $\tilde{\gamma}(\omega_o)$.

Let $H_o$ denote the null hypothesis that a given value of $\tilde{\gamma}(\omega_o)$ is within the hypertensive region and the alternative hypothesis $H_1$ be that $\tilde{\gamma}(\omega_o)$ is within the normotensive region. Let $p_{norm}(\tilde{\gamma}(\omega_o))$ and $p_{hyp}(\tilde{\gamma}(\omega_o))$ be the probability density functions of $\tilde{\gamma}(\omega_o)$ estimated for the normotensive and the hypertensive groups, respectively.

The conditional probability that $\tilde{\gamma}(\omega_o)$ belongs to the null hypothesis is denoted by $$p(\tilde{\gamma}(\omega_o)|H_o) = p_{hyp}(\tilde{\gamma}(\omega_o)).$$

Similarly, we define $$p(\tilde{\gamma}(\omega_o)|H_1) = p_{norm}(\tilde{\gamma}(\omega_o))$$

as the conditional probability the $\tilde{\gamma}(\omega_o)$ belongs to the alternate hypothesis. Then, the threshold of detection $\tilde{\gamma}(\omega_o)$ is chosen such that the cost function $$J = w_1 \int_{-\infty}^{\tilde{\gamma}_{th}(\omega_0)} Phyp(\tilde{\gamma}(\omega_0)) d\tilde{\gamma}(\omega_0) + \omega_2 \int_{\tilde{\gamma}_{th}(\omega_0)}^{\infty} Pnorm(\tilde{\gamma}(\omega_0)) d\tilde{\gamma}(\omega_0),$$

is maximized, where $\omega_1$ and $\omega_2$ are positive weighting constants. Note that the first integral in the above expression represents the sensitivity and the second integral defines the specificity of the algorithm.

At the optimum threshold level $\tilde{\gamma}_{th}(\omega_o)$, $$\frac{\partial J}{\partial \tilde{\gamma}(\omega_0)} = \omega_1 Phyp(\tilde{\gamma}th(\omega_0)) - \omega_2 Pnorm(\tilde{\gamma}th(\omega_0)) = 0,$$

implying that $$\omega_1 Phyp(\tilde{\gamma}th(\omega_0)) = \omega 2 Pnorm(\tilde{\gamma}th(\omega_0)).$$

The solution to the above equation provides the optimum threshold level $\tilde{\gamma}_{th}(\omega_o)$.

Preliminary Studies

In preliminary studies it was assumed that there was no significant variation in the environmental, fetal-umbilical, and maternal-uterine waveform characteristics within short intervals of time. The blood velocity waveforms were recorded sequentially within a 5-minute interval. A delay in one of the signals changes only the phase of the cross-spectrum of the two signals. Since the MSC function contains no information about the relative phase between the two signals, the estimated MSC function from the sequentially acquired data will not show much difference from the estimates obtained from simultaneously acquired data. This assumes that the joint statistics of the two signals do not change during the time frame in which the data were collected.

A total of 44 maternal-fetal data sets were collected during the $10^{th}$ through the $22^{nd}$ week of gestation, of which 34 resulted in normal pregnancy outcome. The rest of the patients (10 data sets) subsequently developed PIH. Transvaginal (5 MHz) and transabdominial (3.75 MHz) Doppler recording methods were used at 10-13 and 14-22 weeks of gestation, respectively. All Doppler studies were performed with the women in the semi-recumbent position and during fetal apnea. The umbilical arterial velocity waveforms were obtained from the free floating loop of the umbilical cord. The angles of incidence of the ultrasound beams in the measurements were less than 20°. The sampling frequency of the blood velocity waveforms was 93.75 samples/sec and each waveform was recorded for approximately 20 seconds.

In estimating the coherence values at the maternal heart rates for each pair of waveforms, first, the mean values of the maternal heart rate was estimated for each waveform as the frequency corresponding to the peak of the amplitude spectrum. The amplitude spectrum was estimated as the absolute value of the Fourier transform estimated over the entire length of the blood velocity waveform. The power spectra estimated over 16 or more 256-sample data segments. Each data segment was overlapped by 75% by the adjacent segment. Then, the MSC values were estimated using the equation: $|\gamma(\omega)|^2 = (|S_{xy}(\omega)|^2)/(S_{xx}(\omega)S_{yy}(\omega))$.

Figure 5:
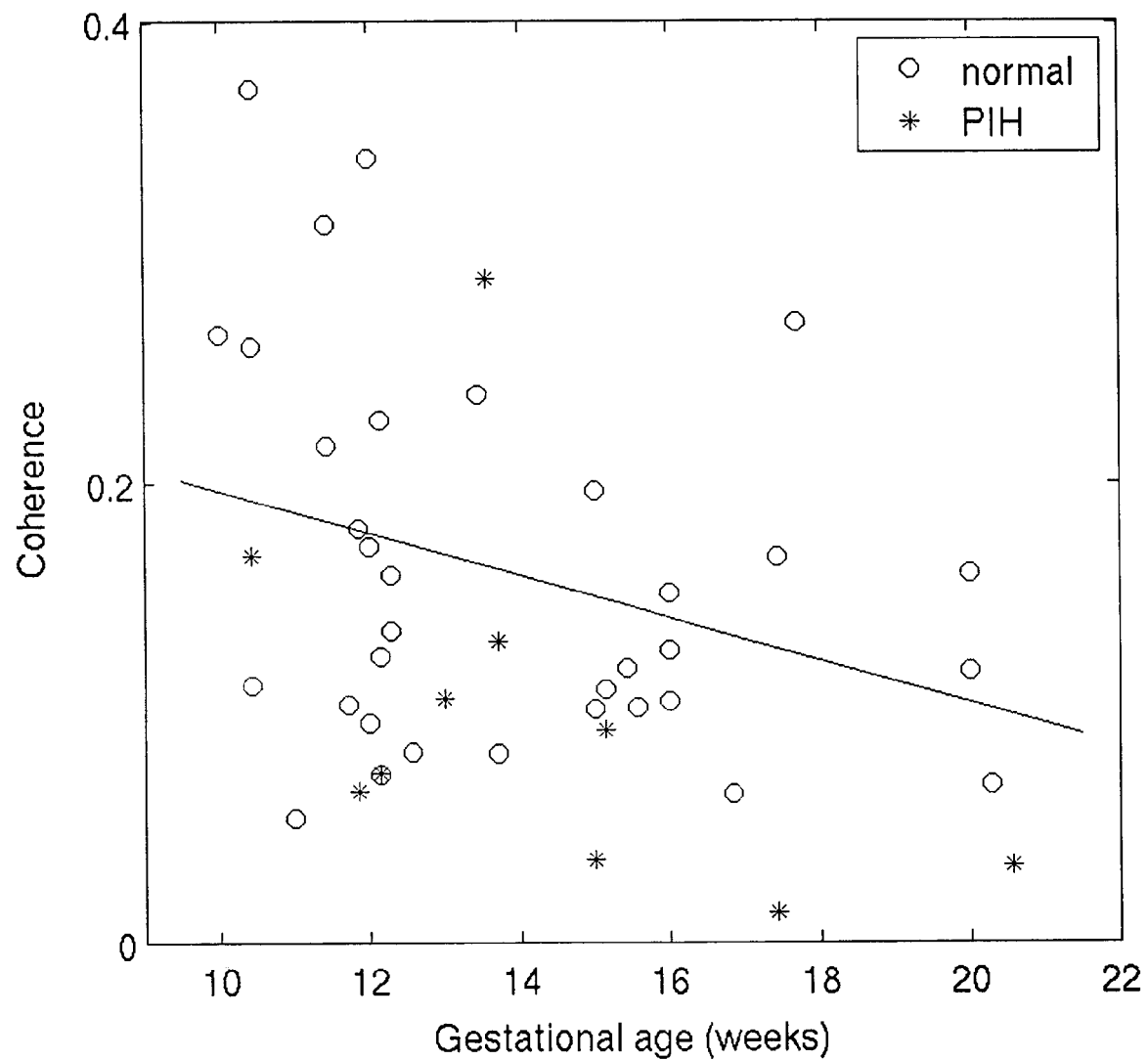
FIG. 5 shows the distribution of the square-root of the MSC function between maternal and fetal arterial blood flow at the maternal heart rate with gestational age.

The distribution of $\gamma(\omega_o)$ is shown in FIG. 5. The open circles denote results for normotenisive pregnancies and asterisks represent the corresponding results for hypertensive pregnancies. The average distribution of $\gamma(\omega_o)$ estimated as a function of the gestational age for normotenisive pregnancies is shown by the solid line in FIG. 5. This curve was obtained using a first order polynomial fit, and satisfies the relationship $$\bar{\gamma}(\omega_0, \theta) = -0.0092\theta + 0.2885,$$

where $\bar{\gamma}(\omega_o, \theta)$ is the mean value of $\gamma(\omega_o)$ at the gestational age $\theta$. FIG. 5 demonstrates that $\gamma(\omega_o)$ values estimated for pregnant women who subsequently developed PIH are in general well below the average for gestational age. Therefore, the average distribution of $\gamma(\omega_o)$ at maternal heart rate can be used as a marker for identifying complicated pregnancies.

Selection of a threshold function to detect pregnancies that may later develop preeclampsia is done using $$\omega_1 Phyp(\tilde{\gamma}th(\omega_0)) = \omega_2 Pnorm(\tilde{\gamma}th(\omega_0)).$$

First, $\tilde{\gamma}(\omega_o)$ values were estimated by subtracting the gestational age dependent mean distribution from $\gamma(\omega_o)$ values. It was assumed that $\tilde{\gamma}(\omega_o)$ in both the normotensive and hypertensive pregnancies belong to truncated Gaussian distributions in the interval $[\tilde{\gamma}_{min}(\omega_o), \tilde{\gamma}_{max}(\omega_o)]$. That is, $$Phyp(\tilde{\gamma}(\omega_0)) = \begin{cases} \frac{1}{C_{hyp}} N(\mu_{hyp}, \sigma_{hyp}^2); & \tilde{\gamma}_{min}(\omega_0) \leq \tilde{\gamma}(\omega_0) \leq \tilde{\gamma}_{max}(\omega_0) \\ 0; & \tilde{\gamma}_{min}(\omega_0) > \tilde{\gamma}(\omega_0) > \tilde{\gamma}_{max}(\omega_0), \end{cases}$$

where $g(\mu_{hyp}, \sigma_{hyp}^2)$ represents a Gaussian density function with mean $\mu_{hyp}$ and variance $\sigma_{hyp}^2$, and $$C_{hyp} = \frac{1}{\sqrt{2\pi\sigma_{hyp}^2}} \int_{\tilde{\gamma}_{mni}(\omega_0)}^{\tilde{\gamma}_{max}(\omega_0)} \exp\left\{-\frac{(\tilde{\gamma}(\omega_0) - \mu_{hyp})^2}{2\sigma_{hyp}^2}\right\} d\tilde{\gamma}(\omega_0).$$

Similarly, $$Pnorm(\tilde{\gamma}(\omega_0)) = \begin{cases} \frac{1}{C_{norm}} N(\mu_{norm}, \sigma_{norm}^2); & \tilde{\gamma}_{min}(\omega_0) \leq \tilde{\gamma}(\omega_0) \leq \tilde{\gamma}_{max}(\omega_0) \\ 0; & \tilde{\gamma}_{min}(\omega_0) > \tilde{\gamma}(\omega_0) > \tilde{\gamma}_{max}(\omega_0) \end{cases},$$

where $C_{norm}$, $\mu_{norm}$ and $\sigma_{norm}^2$ are defined as before for normotensive pregnancies. Substituting the above equations and solving for $\tilde{\gamma}_{th}(\omega_o)$ results in $$\tilde{\gamma}_{th}(\omega_0) = \frac{\sigma_{hyp}^2 \tilde{\gamma}_{norm}(\omega_0) - \sigma_{norm}^2 \tilde{\gamma}_{hyp}(\omega_0) - \sqrt{K}}{\sigma_{hyp}^2 - \sigma_{norm}^2},$$

where $$K = (\sigma_{hyp}^2 \tilde{\gamma}_{norm}(\omega_0) - \sigma_{norm}^2 \tilde{\gamma}_{hyp}(\omega_0))^2 - (\sigma_{hyp}^2 - \sigma_{norm}^2)$$

$$\left(\sigma_{hyp}^2 \tilde{\gamma}_{norm}^2(\omega_0) - \sigma_{norm}^2 \tilde{\gamma}_{hyp}^2(\omega_0) - 2\sigma_{hyp}^2 \sigma_{norm}^2 \ln\left[\frac{\sigma_{hyp}}{\sigma_{norm}} \frac{\omega_2}{\omega_1} \frac{C_{hyp}}{C_{norm}}\right]\right).$$

The mean-removed MSC function at the maternal heart rate ranged from $\tilde{\gamma}_{min}(\omega_o) = -0.15$ to $\tilde{\gamma}_{max}(\omega_o) = 0.2$ for the data used experimentally. The variance and mean values of $\tilde{\gamma}(\omega_o)$ were $\sigma_{norm}^2 = 0.0059$ and $\mu_{norm} = 0$, respectively, for normotensive pregnancies and $\sigma_{hyp}^2 = 0.0046$ and $\mu_{hyp} = -0.00764$, respectively, for hypertensive pregnancies. The results may change for larger test groups.

Figure 6:
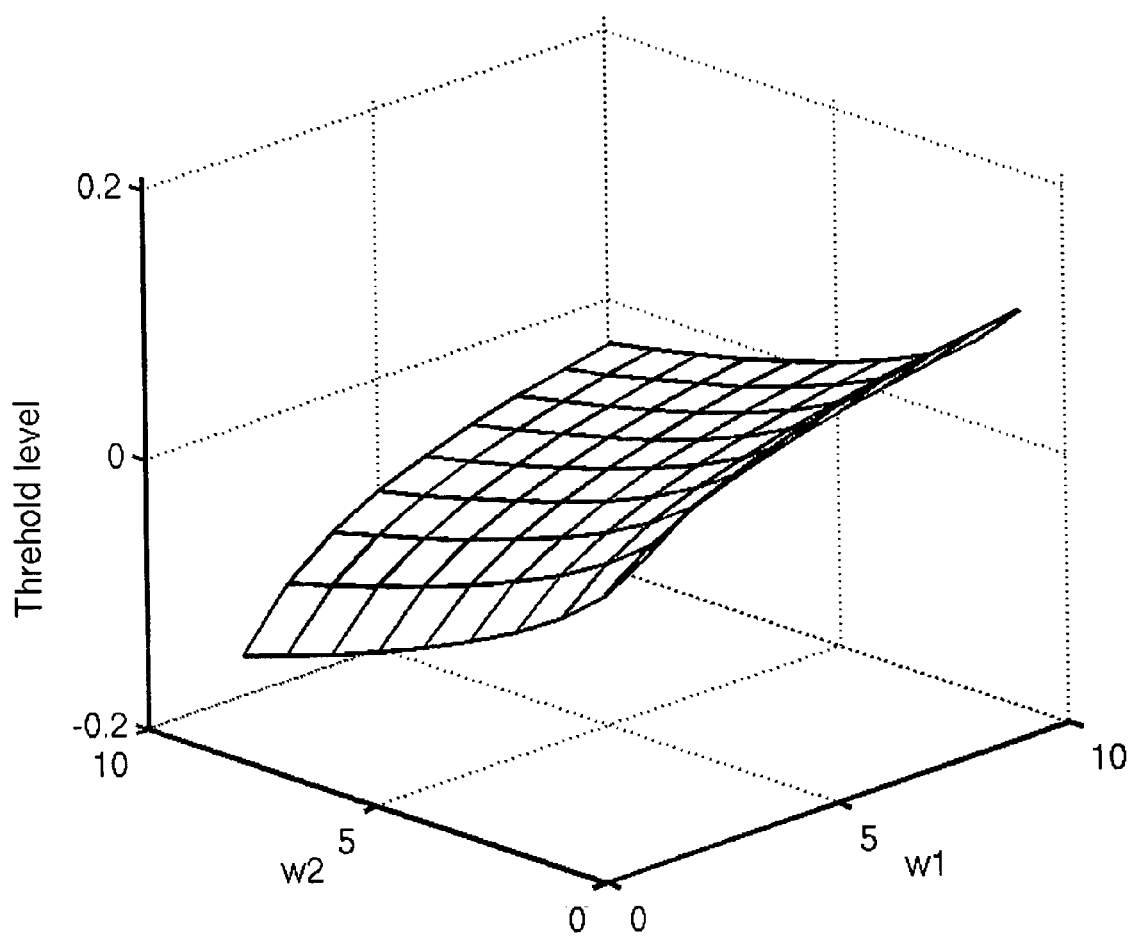
FIG. 6 shows the distribution of the threshold level with weighting constants.
Figure 7:
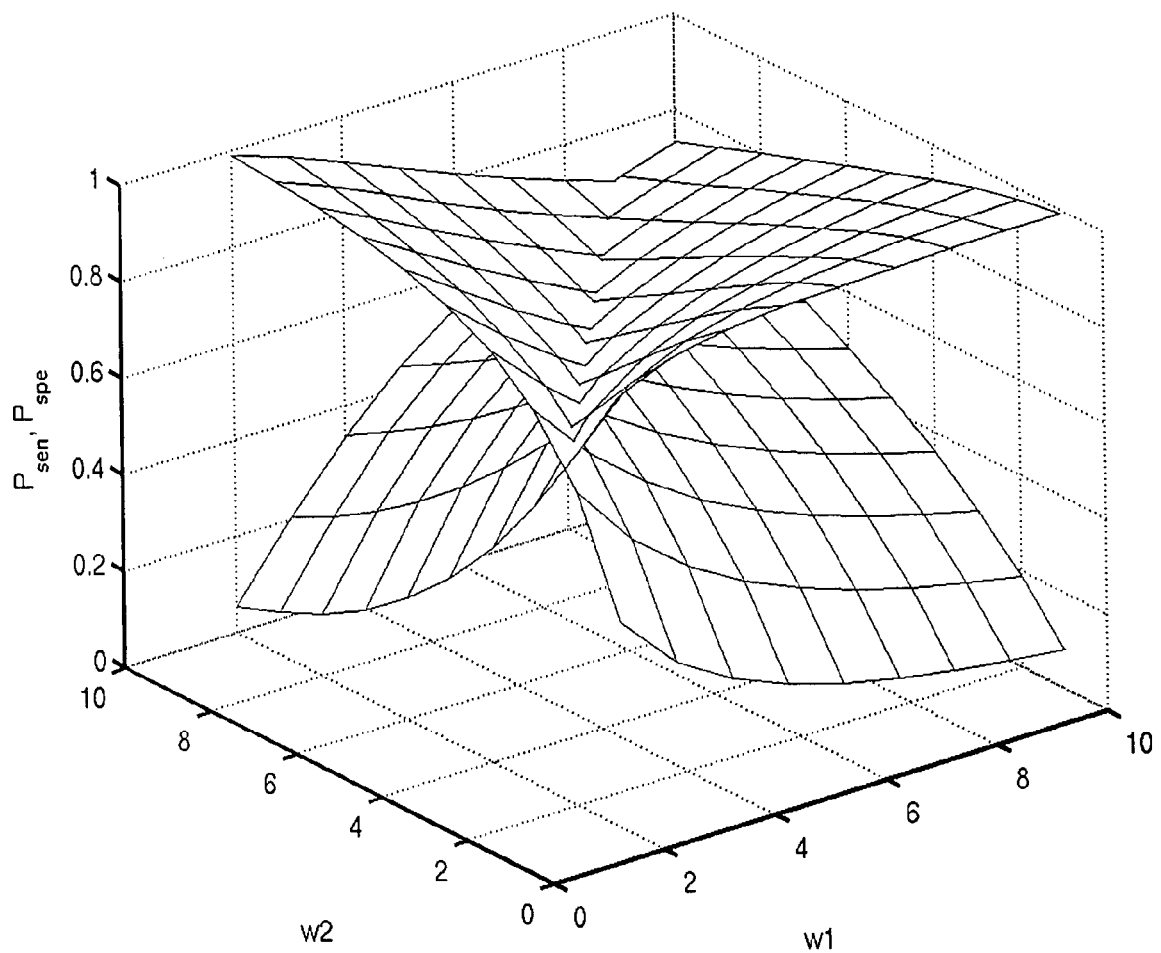
FIG. 7 shows the distribution of the sensitivity and specificity with weighting constants.
Figure 8:
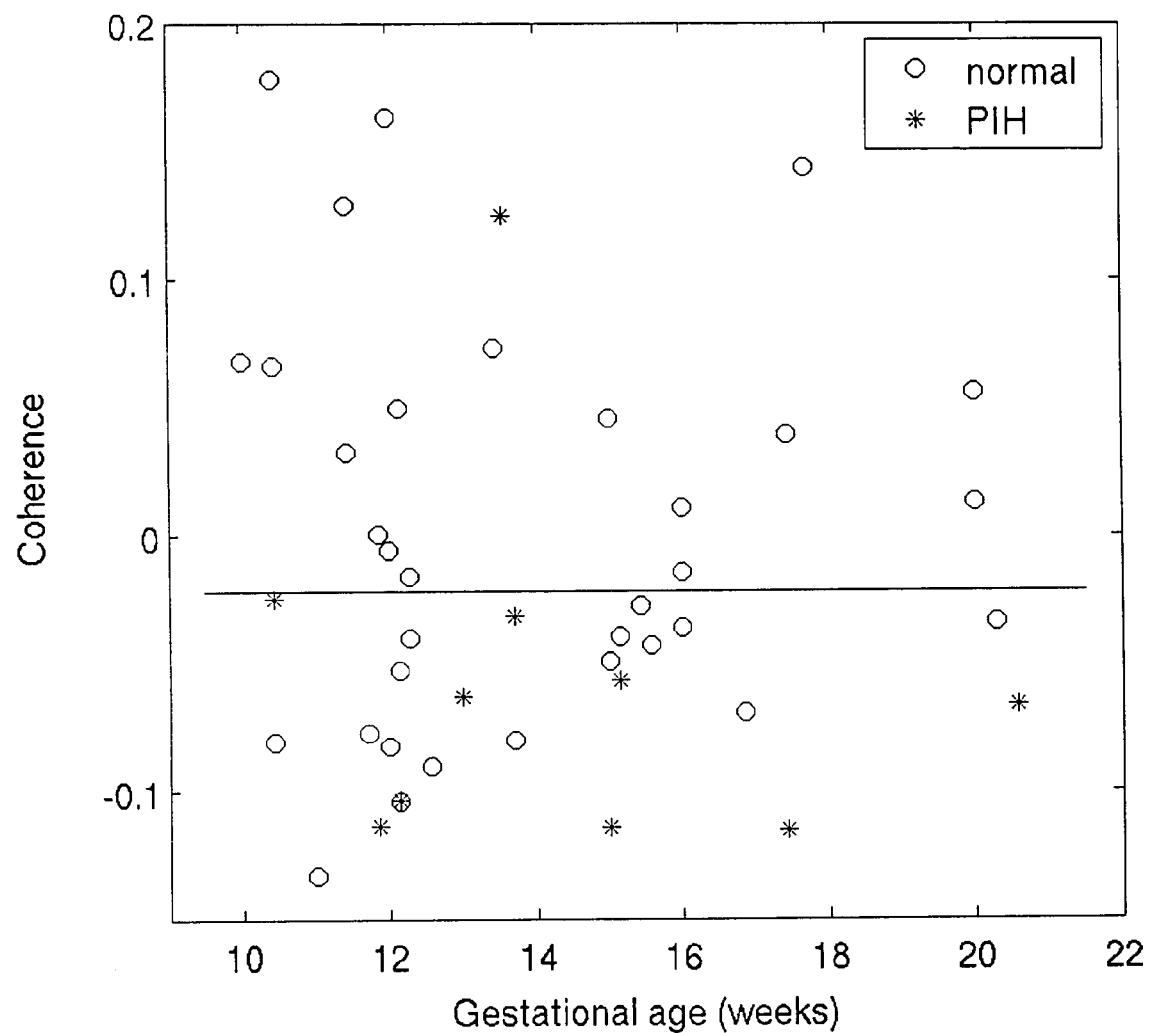
FIG. 8 shows the threshold level and coherence distribution.

The variation of the threshold level $\tilde{\gamma}_{th}(\omega_o)$ estimated using the equations above with various choices of the two weighting factors $\omega_1$ and $\omega_2$ is shown in FIG. 6. With the increase in the $\omega_1$, the weight for sensitivity, the threshold level increases whereas with the increase in $\omega_2$, the weight factor for specificity, the threshold level decreases. The distribution of the sensitivity $P_{sen}$ and specificity $P_{spe}$ are shown in FIG. 7 for the above ranges of $\omega_1$ and $\omega_2$. The distribution of mean-removed coherence values and the threshold level for $\omega_1 = 5$ and $\omega_2 = 4$ is shown in FIG. 8. In the preliminary testing, the optimum threshold level was $-0.0173$. The theoretically calculated sensitivity was 80.03% and the corresponding specificity was 58.11%. The experimentally evaluated sensitivity and specificity of the test were 90% and 52.94%, respectively. With 22.73% prevalence of the condition in the acquired data, the positive predictive value of the test was 36% and the negative predictive value was 94.74%

Although the results stated above were obtained for the data on which the algorithm was trained to select the threshold, in practice, the algorithm should be tested on data that were not employed to train the system. Another round of testing was performed on the data sets to see how well the method works when the training data was not the testing data. Of the original 44 data sets, 34 (27 normal and 7 PIH) were selected to serve as the training data sets and the remaining 10 (7 normal and 3 PIH) were used for testing the method. The mean value and variance of the threshold value, sensitivity and specificity associated with all possible combinations of training and test data sets for $\omega_1 = 5$ and $\omega_2 = 4$, and 80% theoretical sensitivity are displayed in Table I in FIG. 9. The results were close to 80% sensitivity for $\omega_1 = 5$ and $\omega_2 = 4$. With 80% sensitivity, the results were approximately similar. From this, it is expected that the method will perform well in practical situations.

Comparing these results with other available methods that use Doppler ultrasound data reveals the other methods to be unreliable. With respect to using the uterine-arterial pulsatility index (PI), there is no significant variation in the resistance to the uterine arterial blood flow at 10-22 weeks in hypertensive pregnancies from normotensive pregnancies. Also, with respect to the umbilical-arterial blood velocity variability analysis, there was no significant difference in the variance of the blood velocity variability in normotensive and hypertensive pregnancies. Therefore, it appears that neither PI analysis nor blood velocity variability are reliable indicators of subsequent development of preeclampsia.

The main advantages of this coherence analysis for the prediction of preeclampsia are: 1) it can be used to identify women at risk for hypertensive disorders at an earlier stage of pregnancy than currently possible, 2) it is non-invasive and simple to perform, and 3) it is highly sensitive.

The embodiments of the method 100 and apparatus 200 of the present invention may be used to determine other bodily parameters such as, for example and not by way of limitation, maternal and fetal heart rate, HRV and electrocardiogram (EKG). Additionally, the method 100 and apparatus of the present invention may be applied in other circumstances where determining a coherence value relating to two waveforms using a magnitude-squared coherence function and is therefore not limited to predicting preeclampsia. For example, milder forms of the disease such as pregnancy induced hypertension or generally maternal hypertension during pregnancy may also be predicted according to embodiments of the invention described herein.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments of the invention. It will be apparent to those of ordinary skill in the art that numerous modifications can be made without departing from the principles and concepts of the invention as set forth in the claims.

What is claimed is:

1. A system for predicting maternal hypertension during pregnancy, comprising:
    a processor for calculating a coherence value using a magnitude-squared coherence function between a maternal blood velocity waveform and a fetal blood velocity waveform, the magnitude-squared coherence function defined by:

$$|\gamma(\omega)|^2 = (|S_{xy}(\omega)|^2)/(S_{xx}(\omega)S_{yy}(\omega)),$$

wherein $|S_{xy}(\omega)|^2$ is a cross spectrum of the maternal and fetal blood velocity waveforms and $S_{xx}(\omega)$ and $S_{yy}(\omega)$ represent a power spectra of the maternal and fetal blood velocity waveforms;
    a maternal sensor in communication with the processor for measuring the maternal blood velocity waveform;
    a fetal sensor in communication with the processor for measuring the fetal blood velocity waveform, wherein the maternal sensor and the fetal sensor are the same sensor; and
    a comparator configured to compare the coherence value to a predetermined threshold value to identify pregnancies at risk for subsequent hypertension.

2. The system of claim 1, wherein the maternal and fetal sensors are in communication with at least one Doppler ultrasound apparatus.

3. The system of claim 1, wherein the maternal and fetal sensors are Doppler ultrasound sensors.

4. The system of claim 1, wherein the predetermined threshold value can be calculated according to the equation:

$$\omega_1 P_{hyp}(\tilde{\gamma}_{th}(\omega_0)) = \omega_2 P_{norm}(\tilde{\gamma}_{th}(\omega_0)).$$

5. The system of claim 1, wherein the magnitude-squared coherence function can further be used to determine a coherence value between a maternal heart rate and a fetal heart rate.

6. The system of claim 1, wherein the magnitude-squared coherence function can further be used to determine a coherence value between a maternal electrocardiogram and a fetal electrocardiogram.

7. A system for predicting maternal hypertension during pregnancy, comprising:
    a processor for calculating a coherence value using a magnitude-squared coherence function between a maternal blood velocity waveform and a fetal blood velocity waveform, the magnitude-squared coherence function defined by:

$$|\gamma(\omega)|^2 = (|S_{xy}(\omega)|^2)/(S_{xx}(\omega)S_{yy}(\omega)),$$

wherein $|S_{xy}(\omega)|^2$ is a cross spectrum of the maternal and fetal blood velocity waveforms and $S_{xx}(\omega)$ and $S_{yy}(\omega)$ represent a power spectra of the maternal and fetal blood velocity waveforms;
    a maternal sensor in communication with the processor for measuring the maternal blood velocity waveform; and
    a fetal sensor in communication with the processor for measuring the fetal blood velocity waveform;
    a comparator configured to compare the coherence value to a predetermined threshold value to identify pregnancies at risk for subsequent hypertension, wherein the predetermined threshold value can be calculated according to the equation:

$$\omega_1 P_{hyp}(\tilde{\gamma}_{th}(\omega_0)) = \omega_2 P_{norm}(\tilde{\gamma}_{th}(\omega_0)).$$

8. The system of claim 7, wherein the maternal and fetal sensors are in communication with at least one Doppler ultrasound apparatus.

9. The system of claim 7, wherein the magnitude-squared coherence function can further be used to determine a coherence value between a maternal heart rate and a fetal heart rate.

10. The system of claim 7, wherein the magnitude-squared coherence function can further be used to determine a coherence value between a maternal electrocardiogram and a fetal electrocardiogram.

* * * * *

UNITED STATES PATENT AND TRADEMARK OFFICE
CERTIFICATE OF CORRECTION

PATENT NO. : 7,374,539 B2
APPLICATION NO. : 10/934656
DATED : May 20, 2008
INVENTOR(S) : Kumari L. Fernando et al.

It is certified that error appears in the above-identified patent and that said Letters Patent is hereby corrected as shown below:

Title page, item (54) and in col. 1, lines 1-4, correct title by changing "Material" to "Maternal" The title should read as follows:

METHOD AND APPARATUS FOR PREDICTING MATERNAL HYPERTENSION DURING PREGNANCY USING COHERENCE ANALYSIS OF MATERNAL AND FETAL BLOOD VELOCITY WAVEFORMS

Col. 2, line 8 in specification, change "during 1-14 weeks" to read: "during 11-14 weeks"

Col. 15, line 60 in specification, change formula to read " $N(\mu_{hyp}, \sigma^2_{hyp})$ "

Signed and Sealed this

Twenty-fifth Day of November, 2008

JON W. DUDAS
*Director of the United States Patent and Trademark Office*